United States Patent
Haaland

(10) Patent No.: US 9,542,828 B1
(45) Date of Patent: Jan. 10, 2017

(54) SYSTEM, DEVICE, AND METHOD FOR MEASUREMENT OF HAND HYGIENE TECHNIQUE

(71) Applicant: Peter D. Haaland, Fraser, CO (US)

(72) Inventor: Peter D. Haaland, Fraser, CO (US)

(*) Notice: Subject to any disclaimer, the term of this patent is extended or adjusted under 35 U.S.C. 154(b) by 0 days.

(21) Appl. No.: 14/745,754

(22) Filed: Jun. 22, 2015

(51) Int. Cl.
*G08B 21/24* (2006.01)

(52) U.S. Cl.
CPC .................. *G08B 21/245* (2013.01)

(58) Field of Classification Search
CPC ............ G08B 21/245; G08B 13/19684; G08B 15/004; G08B 21/02; G08B 21/0202; G08B 25/016; G08B 25/12
USPC .................................................... 340/539.11
See application file for complete search history.

(56) References Cited

U.S. PATENT DOCUMENTS

| | | | |
|---|---|---|---|
| 5,014,040 A | 5/1991 | Weaver et al. | |
| 5,374,921 A | 12/1994 | Martin et al. | |
| 5,812,059 A | 9/1998 | Shaw et al. | |
| 6,426,701 B1 | 7/2002 | Levy et al. | |
| 6,605,038 B1 | 8/2003 | Teller et al. | |
| 6,727,818 B1 | 4/2004 | Wildman et al. | |
| 7,020,508 B2 | 3/2006 | Stivoric et al. | |
| 7,242,306 B2 | 7/2007 | Wildman et al. | |
| 7,372,367 B2 | 5/2008 | Lane et al. | |
| 7,375,640 B1 | 5/2008 | Plost | |
| 7,770,782 B2 | 8/2010 | Sahud | |
| 7,818,083 B2 | 10/2010 | Glenn et al. | |
| 7,855,651 B2 | 12/2010 | LeBlond et al. | |
| 7,898,407 B2 | 3/2011 | Hufton et al. | |
| 7,978,083 B2 | 7/2011 | Melker et al. | |
| 8,094,029 B2 | 1/2012 | Ortiz et al. | |
| 8,196,810 B2 | 6/2012 | Sahud | |
| 8,237,558 B2 | 8/2012 | Seyed Momen et al. | |
| 8,294,584 B2 | 10/2012 | Plost | |
| 8,344,893 B1 | 1/2013 | Drammeh | |
| 8,395,515 B2 | 3/2013 | Tokhtuev et al. | |
| 8,558,660 B2 | 10/2013 | Nix et al. | |
| 8,587,437 B2 | 11/2013 | Kyle et al. | |
| 8,698,637 B2 | 4/2014 | Raichman | |
| 8,988,240 B2 * | 3/2015 | Burton | A63B 24/0062 340/539.11 |
| 2007/0173705 A1 | 7/2007 | Teller et al. | |
| 2008/0131332 A1 | 6/2008 | Nguyen et al. | |
| 2008/0136649 A1 | 6/2008 | Van De Hey | |
| 2009/0087028 A1 | 4/2009 | Lacey et al. | |
| 2010/0024531 A1 | 2/2010 | Senoo | |
| 2010/0315244 A1 | 12/2010 | Tokhtuev et al. | |
| 2010/0321187 A1 | 12/2010 | Raccio | |
| 2011/0103195 A1 | 5/2011 | Wilbur et al. | |
| 2011/0291840 A1 | 12/2011 | Pelland et al. | |
| 2012/0112906 A1 | 5/2012 | Borke et al. | |

(Continued)

OTHER PUBLICATIONS

Dan Sutch and Tash Lee, Fizzees, futurelab (May 2006).

(Continued)

*Primary Examiner* — Travis Hunnings
*Assistant Examiner* — Omar Casillashernandez
(74) *Attorney, Agent, or Firm* — Michael Best and Friedrich, LLP

(57) ABSTRACT

A device, system, and method for evaluating compliance with a hand hygiene standard using acceleration measurements of the hand or wrist. The method is based on the scalar quantities vigor and/or rocking angle.

13 Claims, 13 Drawing Sheets

Not compliant with WHO standard

(56) References Cited

U.S. PATENT DOCUMENTS

| | | |
|---|---|---|
| 2013/0027199 A1 | 1/2013 | Bonner |
| 2014/0266692 A1* | 9/2014 | Freedman ............ G08B 21/245 340/539.11 |
| 2015/0035678 A1 | 2/2015 | Long |
| 2015/0048940 A1 | 2/2015 | Keown et al. |
| 2015/0134357 A1 | 5/2015 | Davis et al. |
| 2015/0194043 A1 | 7/2015 | Dunn et al. |

OTHER PUBLICATIONS

Ince, N.F. et al., "Detection of Early Morning Daily Activities with Static Home and Wearable Wireless Sensors," EURASIP Journal on Advances in Signal Processing, vol. 2008 (Jul. 17, 2007).

Healthsense eNeighbor Remote Monitoring web page: http://www.healthsense.com/index.php/products/eneighbor-remote-monitoring, publicly available prior to (Mar. 27, 2012).

Keshnet, "Applications of the definite integral to velocities and rates," http://www.ugrad.math.ubc.ca/coursedoc/math103/site2010/keshet.notes/Chapter4.pdf, available prior to Jun. 22, 2015.

U.S. Office action for U.S. Appl. No. 14/849,241 dated Nov. 9, 2015.

U.S. Office action for U.S. Appl. No. 14/849,241 dated Apr. 15, 2016.

PCT Search Report and Written Opinion for International Application No. PCT/US2016/037438 dated Oct. 18, 2016.

* cited by examiner

Note mean compliant 51deg, mean non-compliant 29 degrees

SYSTEM, DEVICE, AND METHOD FOR MEASUREMENT OF HAND HYGIENE TECHNIQUE

BACKGROUND OF THE INVENTION

Inadequate hand hygiene is widely recognized as contributing to the spread of infectious diseases in health care, food preparation, recreational cruising, and other enterprises. Until the invention described here, no method or apparatus has been described that quantifies hand hygiene activity in a way that permits the evaluation of whether the activity meets a pre-determined standard of hand hygiene.

SUMMARY OF THE INVENTION

The invention described below comprises methods and apparatuses for quantifying hand hygiene activity so as to enable the determination of whether that activity complies with pre-determined standards for hand hygiene that are not necessarily established in the form of discrete quantities. The embodiments described herein relate generally to systems and methods for analysis and evaluation of compliance with a predetermined hand hygiene standard based on accelerometer measurements that yield quantitative values identified as vigor and rocking angle. These values quantify the extent of the hand hygiene activity so as to allow a definitive comparison between a pre-determined standard and the activity being monitored. In one example, the standard used to determine hand hygiene compliance is the World Health Organization's (WHO) Guidelines on Hand Hygiene in Health Care (ISBN 978 92 4 159790 6) published in 2009. In another example, the standard used to determine hand hygiene compliance is the Centers for Disease Control's (CDC) Guideline for Hand Hygiene in Health-Care Settings in their Morbidity and Mortality Weekly Report (Oct. 25, 2002/Vol. 51/No. RR-16).

One embodiment provides a method of determining compliance with a standard for hand hygiene technique through analysis of data acquired from one or more wrist-worn accelerometers. The method utilizes vigor or rocking angle or both to determine whether a hand hygiene event complies with a specified standard, such as the WHO or CDC guidelines.

According to one embodiment, an accelerometer is attached to one wrist of a subject to record the instantaneous acceleration experienced by that wrist. Acceleration values $\vec{a}(t)$ are used to determine scalar vigor $v(t)$ and rocking angle $r(t)$ values when executing hand hygiene motions that are compliant with a specified hand hygiene standard. Additional reference measurements are recorded for hand hygiene motions that do not comply with the standard. A classification of hygiene events as compliant or non-compliant is then derived from the differences in vigor and rocking angle values observed for compliant and non-compliant reference measurements.

In one embodiment, the invention provides a device for monitoring hand hygiene. The device comprises a housing configured to be worn on a user's wrist, the housing including an accelerometer configured to measure acceleration of the user's wrist along three axes of motion; and a processing unit in communication with the accelerometer. The processing unit is configured to receive a plurality of the acceleration measurements taken over a period of time during a hand hygiene event carried out by the user, determine vigor values from the plurality of acceleration measurements, compare the vigor values to a vigor threshold based on a hand hygiene standard, determine if one or more of the vigor values meets the vigor threshold, and alert the user to a result of the comparison of the vigor values to the vigor threshold.

In another embodiment, the invention provides a device for monitoring hand hygiene. The device comprises a housing configured to be worn on a user's wrist, the housing including an accelerometer configured to measure acceleration of the user's wrist along three axes of motion; and a processing unit in communication with the accelerometer. The processing unit is configured to receive a plurality of the acceleration measurements taken over a period of time during a hand hygiene event carried out by the user, determine rocking angle values from the plurality of acceleration values, compare the rocking angle values to a rocking angle threshold based on a hand hygiene standard, determine if one or more of the rocking angle values meets the rocking angle threshold, and alert the user to a result of the comparison of the rocking angle values to the rocking angle threshold.

In a further embodiment, the invention provides a system for monitoring hand hygiene. The system comprises a plurality of hand hygiene stations, each station including a RFID tag having a unique identification; a device worn on a user's wrist, the device including a RFID tag reader and an accelerometer; and a computer processor. The computer processor is configured to receive acceleration data from the device associated with a hand hygiene event at one of the hand hygiene stations, determine vigor values or rocking angle values associated with the user's hand hygiene event from the acceleration data, determine if the vigor values or the rocking angle values associated with the hand hygiene event satisfies a standard for hand hygiene technique, transmit a first notification to the user if the hand hygiene event satisfies the standard, and transmit a second notification to the user if the hand hygiene event does not satisfy the standard.

In yet another embodiment, the invention provides a method of evaluating compliance with a hygiene standard. The method comprises measuring acceleration with an accelerometer applied to one or more of hands, wrists, or forearms during events that comply with the standard; measuring acceleration with an accelerometer applied to one or one or more of hands, wrists, or forearms during events that do not comply with the standard; determining at least one vigor value for compliant events; determining at least one vigor value for non-compliant events; and comparing at least one of the vigor values for compliant events and vigor values for non-compliant events to establish whether compliance is achieved in subsequent events.

In another embodiment, the invention provides a method of evaluating compliance with a hygiene standard. The method comprises measuring acceleration with an accelerometer applied to one or more of hands, wrists, or forearms during events that comply with the standard; measuring acceleration with an accelerometer applied to one or one or more of hands, wrists, or forearms during events that do not comply with the standard; determining at least one rocking angle value for compliant events; determining at least one rocking angle value for non-compliant events; and comparing at least one of the rocking angle values for compliant events and rocking angle values for non-compliant events to establish whether compliance is achieved in subsequent events.

Another embodiment uses one of a threshold vigor level or a threshold rocking angle range to establish compliance with a predetermined hand hygiene standard.

Yet another embodiment uses the derivative of vigor with respect to time to characterize compliant versus non-compliant hand hygiene motions or technique.

Yet another embodiment compares the distribution of rocking angles over a time interval to characterize compliant versus non-compliant hand hygiene motions or technique.

Yet another embodiment evaluates vigor, rocking angle, or both on two wrists simultaneously to establish criteria for compliance with a predetermined hand hygiene standard.

Yet another embodiment uses vigor, rocking angle, or a combination thereof and the WHO consensus guidelines for proper hand hygiene to establish thresholds for acceptable technique.

Yet another embodiment specifies a hand hygiene standard with pairs of at least one of (vigor, time) or (rocking angle, time) targets within which a complex pattern of hand hygiene motions are established.

Other aspects of the invention will become apparent by consideration of the detailed description and accompanying drawings.

DETAILED DESCRIPTION

Figure 1:
FIG. 1 is a series of diagrams illustrating steps required to comply with the World Health Organization's consensus standards for proper hand hygiene using alcohol-based sanitizer.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

The terms "first," "second," "third," and the like, as used herein, do not denote any order, quantity, or importance, but rather are used to distinguish one element from another.

Inactivating infectious agents from a person's hand surfaces requires application of a cleaning or disinfecting composition over the whole surface of both hands for enough time to ensure complete reaction of the composition with the agents. Cleaning compositions include surfactants, soaps, and abrasives, while disinfectants include alcohol-based sanitizers, lotions with germicidal additives, and the like. The Centers for Disease Control (CDC) established its Guideline for Hand Hygiene in Health-Care Settings in their Morbidity and Mortality Weekly Report (Oct. 25, 2002/Vol. 51/No. RR-16) and the World Health Organization (WHO) published its Guidelines on Hand Hygiene in Health Care (ISBN 978 92 4 159790 6) in 2009. The latter guidelines, which provide consensus recommendations for hand hygiene using sanitizer or soap and water, are summarized in FIGS. 1 and 2.

Figure 2:
FIG. 2 is a series of diagrams illustrating steps required to comply with the World Health Organization's consensus standards for proper hand hygiene using soap and water.

As noted above, the WHO has provided guidelines illustrated in FIGS. 1 and 2 for proper hand hygiene techniques. The WHO guidelines are pictorial in nature and subject to varying interpretations on how proper hand hygiene should be performed. In one embodiment, the invention involves development of a method to quantify the hand motions in order to evaluate whether the hand motions during a hand hygiene event are in compliance with the pictorial hand motions shown in the WHO guidelines. The method also can be applied to other hand hygiene standards to quantify hand motions to evaluate compliance with the standard. An embodiment of the invention also provides a device and a system that utilizes algorithms relating to vigor and rocking angle to assist users, when performing a hand hygiene event, in knowing whether their hand motions are in compliance with a standard, such as the WHO guidelines (or other standard or guidelines).

A hand hygiene event involves the application of pressure by a person to his or her hands to work the cleanser or disinfecting composition into the outer layers of the hands' epidermis and to move their hands with respect to one another to ensure all exposed skin surfaces (e.g., palms, fingers, and backs of the hands) are wetted by the composition. Since pressure is force per unit area and force is mass times acceleration, the center of mass of the person's hands is subject to acceleration during such a hand hygiene event. Each wrist is mechanically connected to the center of mass of each hand so that the wrist also experiences acceleration from the hand motion that occurs during the hygiene event. The wrist also experiences steady acceleration of 1 g from the earth's gravity; this acceleration vector is oriented vertically, toward the center of the earth.

The user's hand motions during a hand hygiene event can be quantified by applying an accelerometer to the user's wrist and collecting acceleration data during the hand hygiene event. The acceleration data can be used to determine a vigor value and a rocking angle value. The vigor value generally represents the intensity of the hand motion, and the rocking angle value generally represents the extent of the rotation of the hand motion. Thus, either or both of the vigor and rocking angle values can be used as explained below to quantify the quality or characteristics of a person's hand washing motions during a hand hygiene event and compare the hand hygiene event to a predetermined hygiene standard.

Acceleration $\vec{a}$, is used herein to denote the instantaneous acceleration that results from all forces on the hand according to Newton's law a=F/m, where F is the net force exerted on the pair of hands transmitted to the site of an accelerometer or gyroscope affixed to the hand, wrist, or forearm.

The acceleration values $\vec{a}(t)$ are used to determine vigor values and rocking angle values. Vigor, as described herein, is a scalar quantity that does not explicitly measure the orientation of the hands during hygiene events. A scalar quantity, vigor v, is defined as the integral over time of the norm of the derivative with respect to time of the vector $\vec{a}$, the instantaneous acceleration:

$$v(t) = \int_0^t \left| \frac{d\vec{a}}{dt} \right| dt$$

where the $\|$ indicate the vector norm of the enclosed quantity. For discrete measurements of acceleration separated by a time $\delta t$ and components $\vec{a}(t)=(a_x(t), a_y(t), a_z(t))$ a finite difference approximation $$\left| \frac{d\vec{a}}{dt} \right| = \frac{1}{\delta t} \sqrt{(a_x(t+\delta t) - a_x(t))^2 + (a_y(t+\delta t) - a_y(t))^2, (a_z(t+\delta t) - a_z(t))^2}$$

may be substituted for the differential form.

Rocking angle, as described herein, is a second scalar quantity that is a measure of rotation that can be determined from the same accelerometer data used to compute vigor. See FIGS. 1 and 2 where several of the required motions involve rotation. Rocking angle, as defined herein is $$r(t) = \cos^{-1}\left( \frac{\overline{a(t)}}{|a(t)|} \cdot \left\langle \frac{\overline{a(t)}}{|a(t)|} \right\rangle \right)$$

which is a measure of angular displacement using the average value $$\left\langle \frac{\overline{a(t)}}{|a(t)|} \right\rangle$$

of the acceleration $\vec{a}(t)$ over a suitable interval T as an angular reference direction. The argument of the inverse cosine function in this definition is the inner or dot product of the two vector quantities and $\|$ symbols indicate the scalar norm of the enclosed vector quantity.

Figure 3:
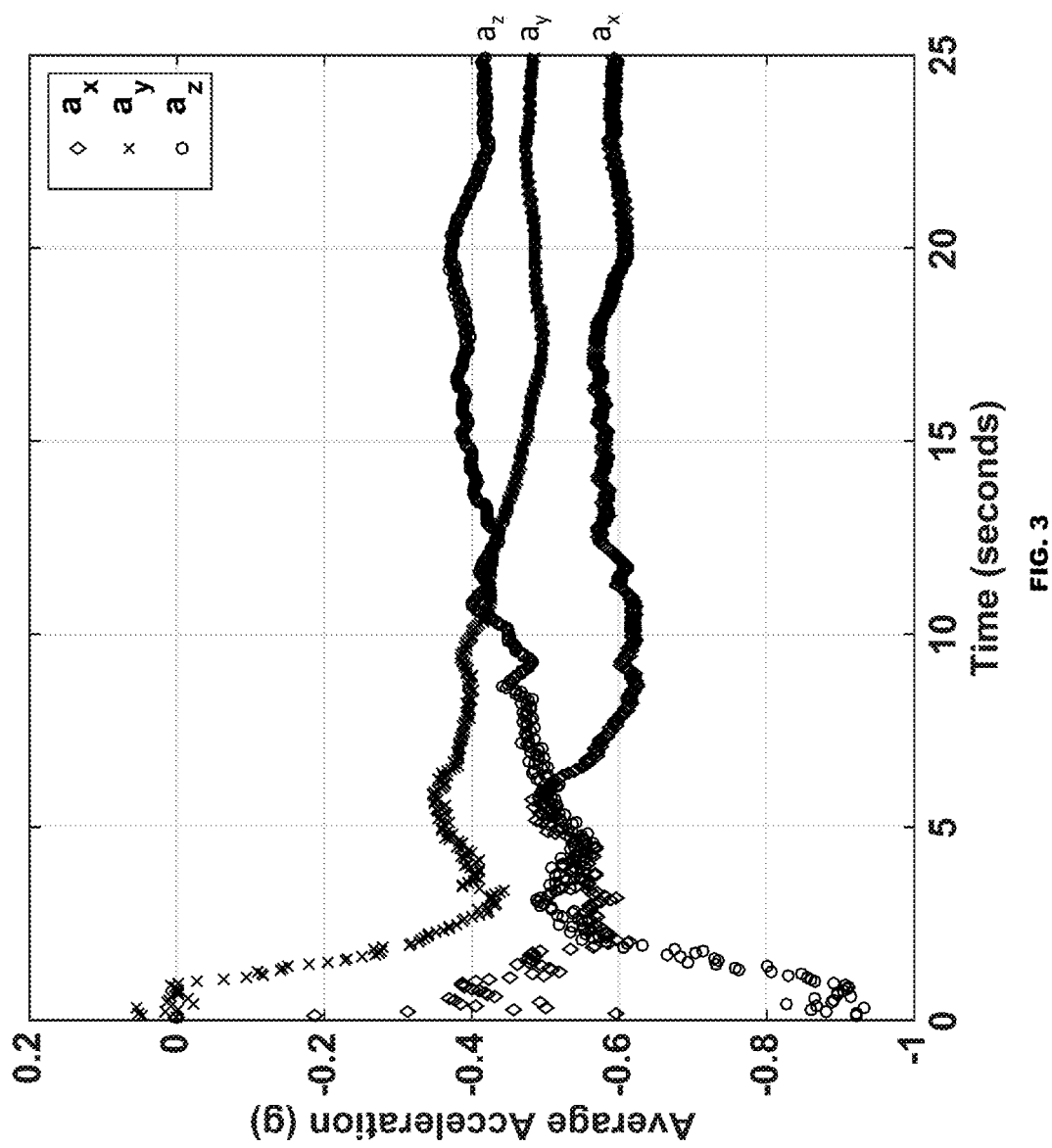
FIG. 3 shows convergence of the average values for the x, y, and z components of acceleration that provide the basis of a stable reference vector direction for calculation of the rocking angles. The ordinate shows the time over which discrete accelerometer values are averaged.

Because the orientation of the accelerometer with respect to vertical is unknown, the reference for the rocking angle calculation is taken as an average angle, measured in the accelerometer's frame of reference, for a series of samples. Referring to FIG. 3, the averages of each of three components of acceleration measured during a sample hand hygiene motion are displayed as a function of the time over which the average is computed. Although the instantaneous orientation of the acceleration vector varies widely, the average values converge within 3-5 seconds to account for the direction of the primary constant in the system, namely the orientation of the earth's gravitational acceleration vector. Using this as an example, the $$\left\langle \frac{\overline{a(t)}}{|a(t)|} \right\rangle$$

would be a vector of unit length oriented with (−0.7015, −0.5378, −0.4677) in the reference frame of the accelerometer.

In general, the orientation of the accelerometer with respect to vertical is unknown, so a series of accelerometer readings will each have a contribution from gravity added to the acceleration resulting from mechanical forces applied to the hands. Vigor and rocking angle, as defined herein, are agnostic with respect to the accelerometer's initial orientation and therefore measure hand motion directly, as will be apparent from the following.

Figure 4:
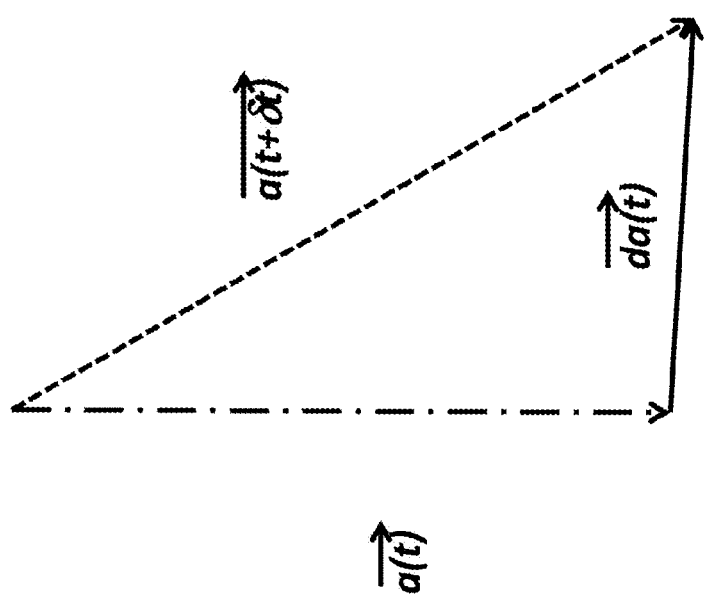
FIG. 4 illustrates the geometric relationship between the acceleration vectors measured by an accelerometer at two discrete times, t and t+δt, and the vector displacement d $\vec{a}$.

Referring to FIG. 4, at times t and t+δt the acceleration vector changes from $\vec{a}(t)$ to $\vec{a}(t+\delta t)$. The vector difference between these two accelerations, $\vec{da}(t)$ has both magnitude and direction. The incremental contribution to vigor is defined as the scalar length or norm of this, $|\vec{da}(t)|$ and the vigor is the integral of this contribution over time:

$$v(t) = \int_0^t \left|\frac{d\vec{a}}{dt}\right| dt.$$

The dimension of vigor is units of acceleration (meter per second ($m*s^{-2}$) or Newtons per kilogram ($N*kg^{-1}$)); with reference to the acceleration from earth's gravity, g; 1 g=9.80665 $m*s^{-2}$=9.80665 $N*kg^{-1}$.

EXAMPLES

In view of the above discussion relating to the development of vigor and rocking angle, test subjects were gathered and asked to perform hand hygiene events. To quantify hand motions based on a standard (e.g., the WHO standard or the CDC standard), test subjects applied an accelerometer to their wrists and were asked to perform hand hygiene motions that comply with the standard and hand hygiene events that do not comply with the standard. The accelerometer is embodied as a device described below, and the accelerometer data was acquired over time during the hand hygiene event and saved in memory.

For example, the test subjects were asked to follow the steps in the WHO guidelines in any order. Test subjects (with an applied accelerometer on their wrists) were asked to perform hand hygiene motions that did not comply with the standard. For example, the test subjects were asked to skip one of the steps in the WHO standard or were asked to perform a step modified from that specified in the WHO standard. In one example, five test subjects each performed 40 trials of a series of hand hygiene motions that each complied with the standard ("the compliant trials"), and the same five test subjects each performed 40 trials of a series of hand hygiene motions where at least one of the motions did not comply with the standard ("the non-compliant trials").

Figure 5:
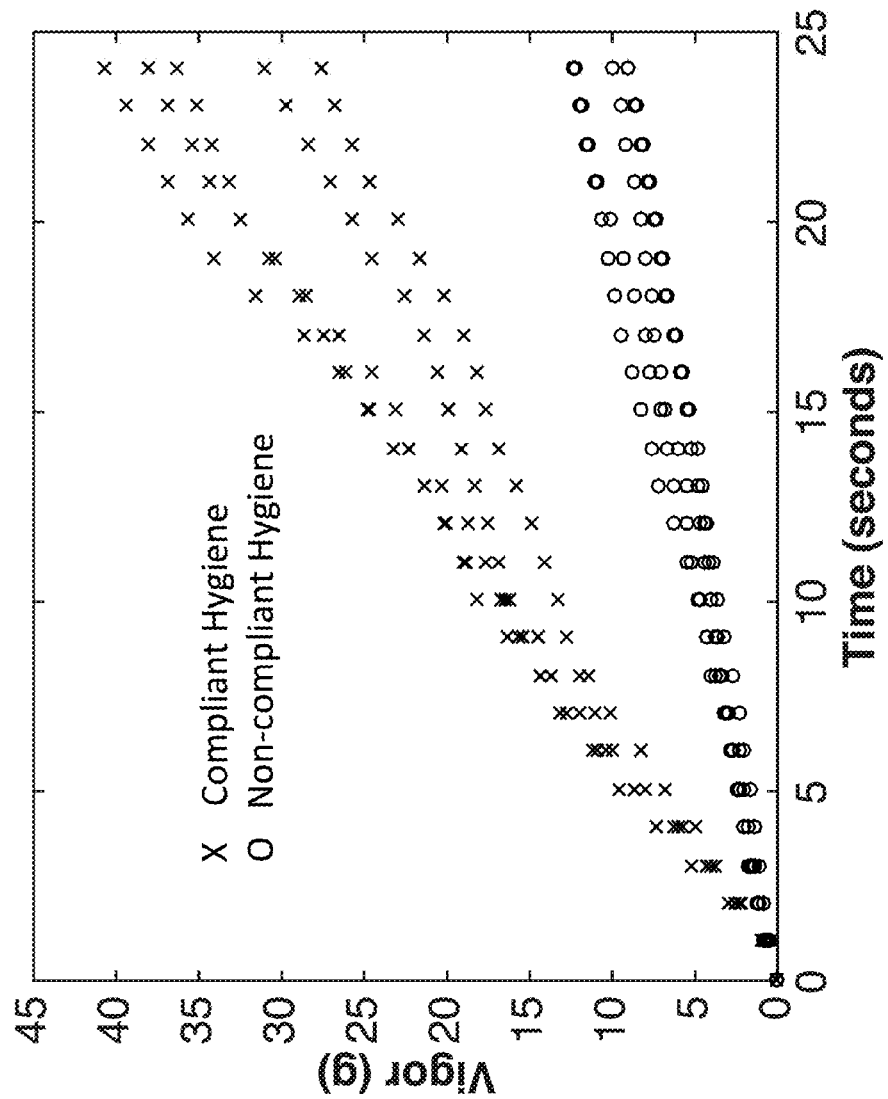
FIG. 5 displays ten sets of vigor values computed from accelerometer measurements at 50 millisecond intervals, five each while executing proper (x) and improper (o) hand hygiene technique according to the steps illustrated in FIG. 1. The plot displays every $10^{th}$ value for visual clarity. Units of acceleration are g; 1 g=9.80665 m*s$^{-2}$.
Figure 6:
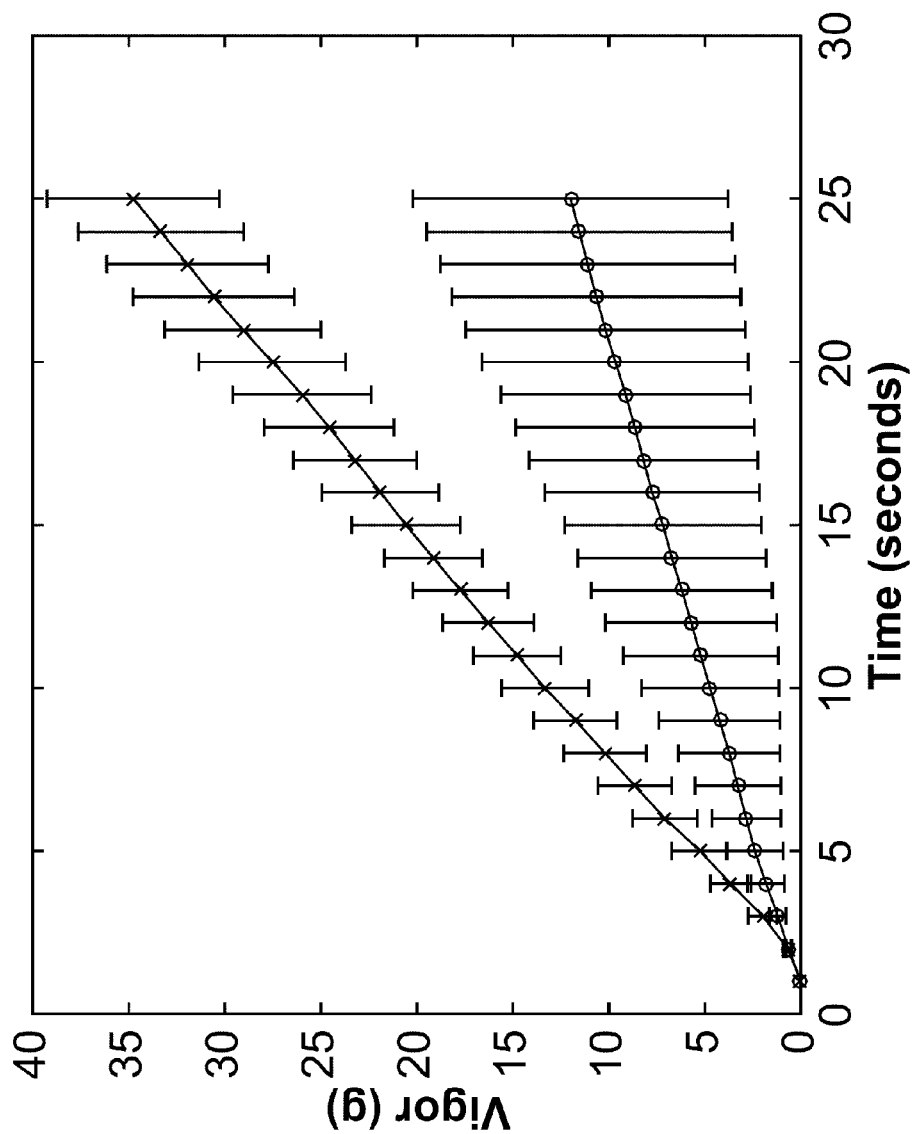
FIG. 6 graphically illustrates the average vigor values obtained for twenty compliant (x) and twenty non-compliant (o) hygiene motions or actions with error bars set at +/−1 standard deviation of the measured values.

The accelerometer data from all the test subjects was collected. The accelerometer data for each test subject was applied to the algorithm for vigor and the algorithm for rocking angle. The resulting vigor values and rocking angle values were graphically plotted. A typical record of vigor as a function of time for hand hygiene motions that complied with the WHO standard is shown as x symbols in FIG. 5, and records for non-compliant hand hygiene motions are displayed as o in the same figure. Variability of the vigor profiles when executing hand hygiene motions in accordance with technique that follows specific guidelines is natural for individuals cleaning or disinfecting their hands. FIG. 6 displays the mean vigor and its standard deviation for compliant (x) and non-compliant (o) hand hygiene motions for one test subject. Although the mean values are separated within about 5 seconds, their difference, and therefore the ability to distinguish compliant from non-compliant motions using vigor, increases with time.

Figure 7:
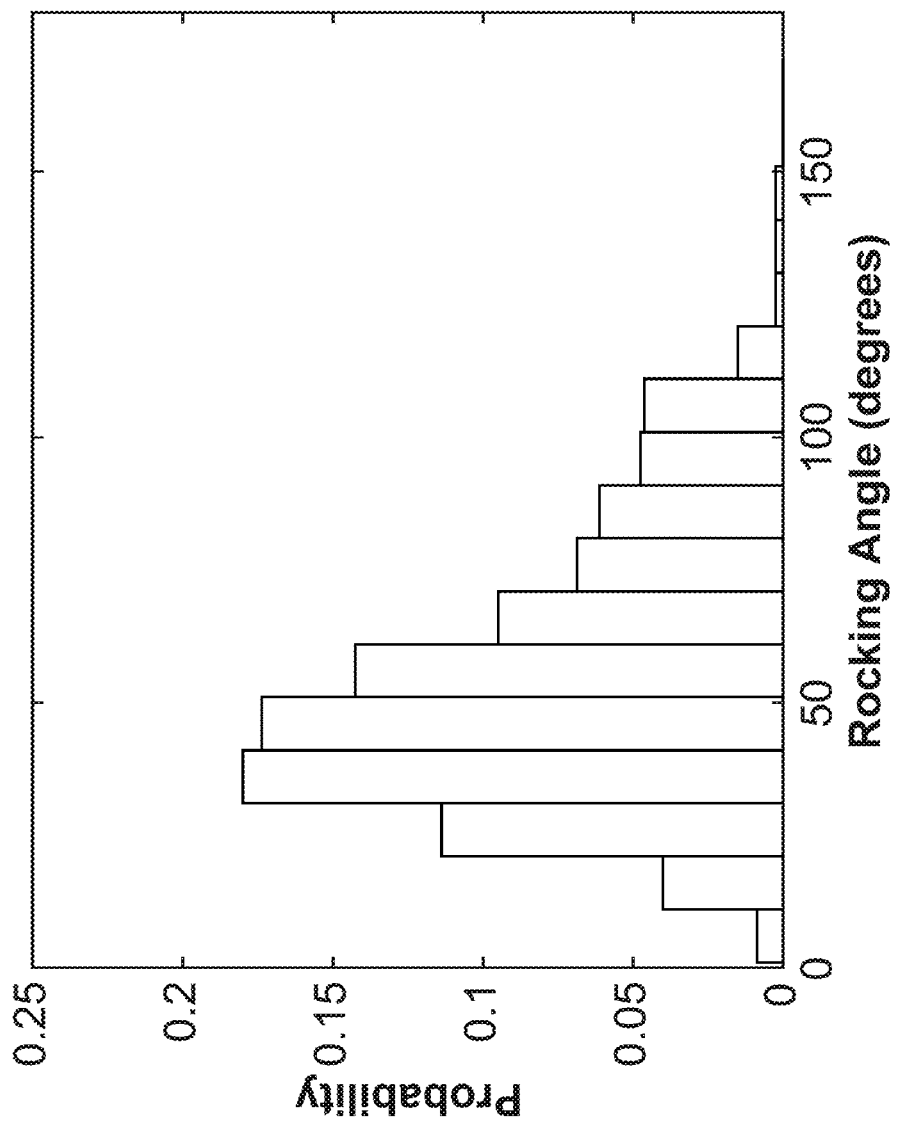
FIG. 7 is a histogram of rocking angles for twenty, 25-second hand motions that comply with the WHO hand hygiene standard.
Figure 8:
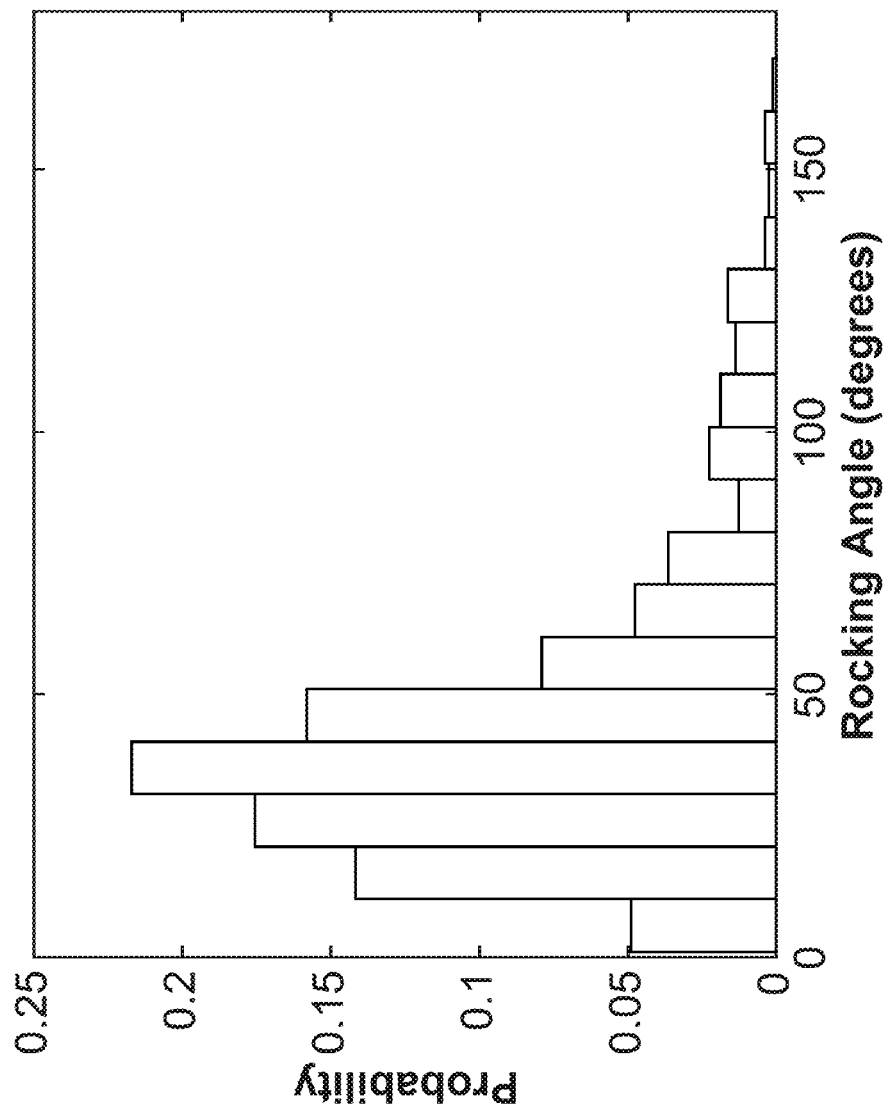
FIG. 8 is a histogram of rocking angles for twenty, 25-second hand motions that do not comply with the WHO hand hygiene standard.
Figure 9:
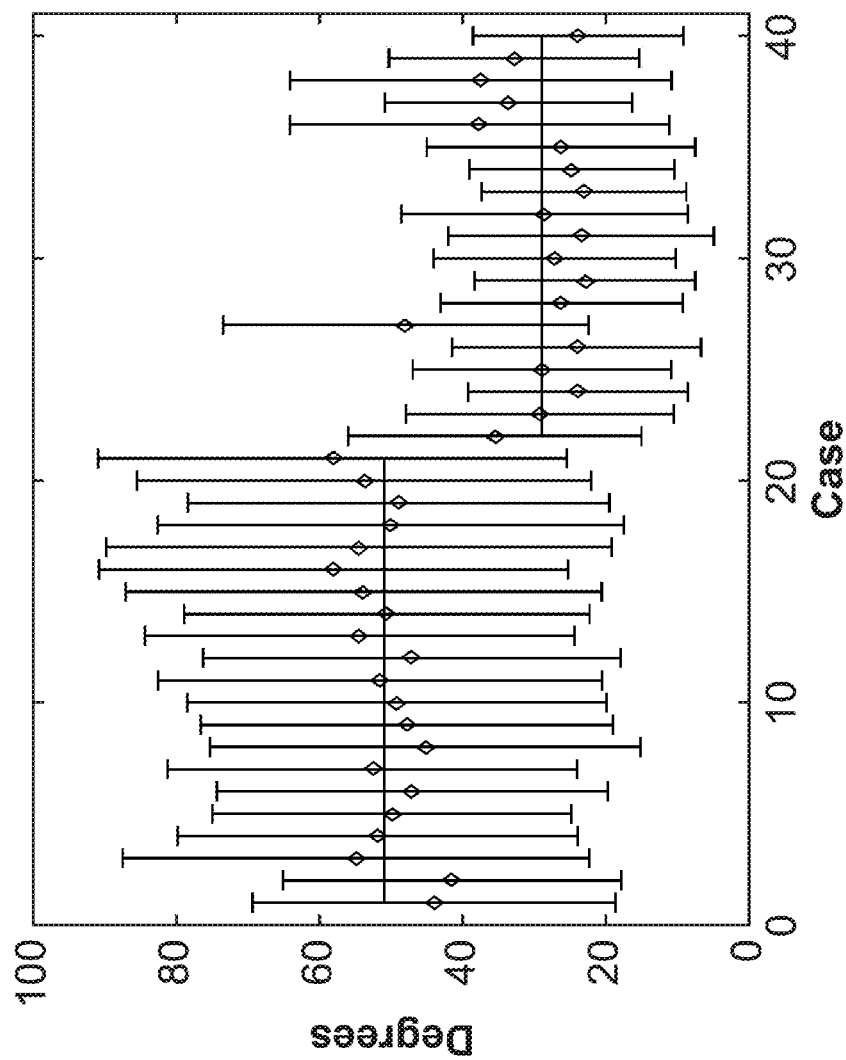
FIG. 9 shows the mean rocking angles for forty sets of hand motion; the first 21 are for events that comply with the WHO hand hygiene standard, the last 19 events do not comply with the standard. Error bars indicate +/−1 standard deviation from the mean vigor values.

The range of rocking angles determined for hand hygiene events that complied with the WHO guidelines are shown in the histogram in FIG. 7, and those for non-compliant technique are in FIG. 8. The average values and standard deviations for 21 compliant events and 19 non-compliant events are shown in FIG. 9. Referring to these figures, both the average rocking angle and the variability of rocking angle are substantially greater for wrist motion that follows the WHO hygiene standard. The rocking angles shown in FIGS. 3 and 11-13 and the vigor values shown in FIGS. 5 and 6 were determined from the same set of accelerometer measurements of hand hygiene. The same procedures can be used for determining compliance with other types of hand hygiene standards.

Based on the difference in the average values for vigor and rocking angle between the compliant trials and the non-compliant trials, a threshold for vigor and a threshold for rocking angle can be defined to which future hand hygiene events can be compared. Using the testing methodology noted above, a threshold for vigor and rocking angle can be established based on an individual's hand hygiene technique. Rather than using a group of individuals to establish the thresholds for vigor and rocking angle, multiple trials with a single individual can be used to establish a threshold for a particular individual. The selected threshold for vigor and rocking angle can depend on different factors and environmental conditions that influence compliance. The testing methodology for establishing a threshold can be tailored to each individual, group of individuals or applications in which hand hygiene is monitored. For example, the selected thresholds can be different in a restaurant and a hospital. As another example, the selected thresholds for an individual can be based on individual factors such as body mass or other physiological parameters that differ from person to person.

The method of determining acceleration and calculating, and comparing vigor values for motions that do and do not meet a predetermined hand hygiene standard can be replicated for various types of hand motion. For example, it may be desirable to require different types of hand motion for applying sanitizer than for applying soap and water. This is already suggested in the WHO standards for hand hygiene technique shown in FIG. 1 and FIG. 2. Vigor levels may differ significantly for applying compositions, rinsing under running water, and drying with a towel. Applying lotions may require yet another pattern of vigor. These and other applications known to those of ordinary skill in the art of hygiene, where relative hand motion is linked to a predetermined standard, are amenable to treatment according to the methods described herein.

Figure 10:
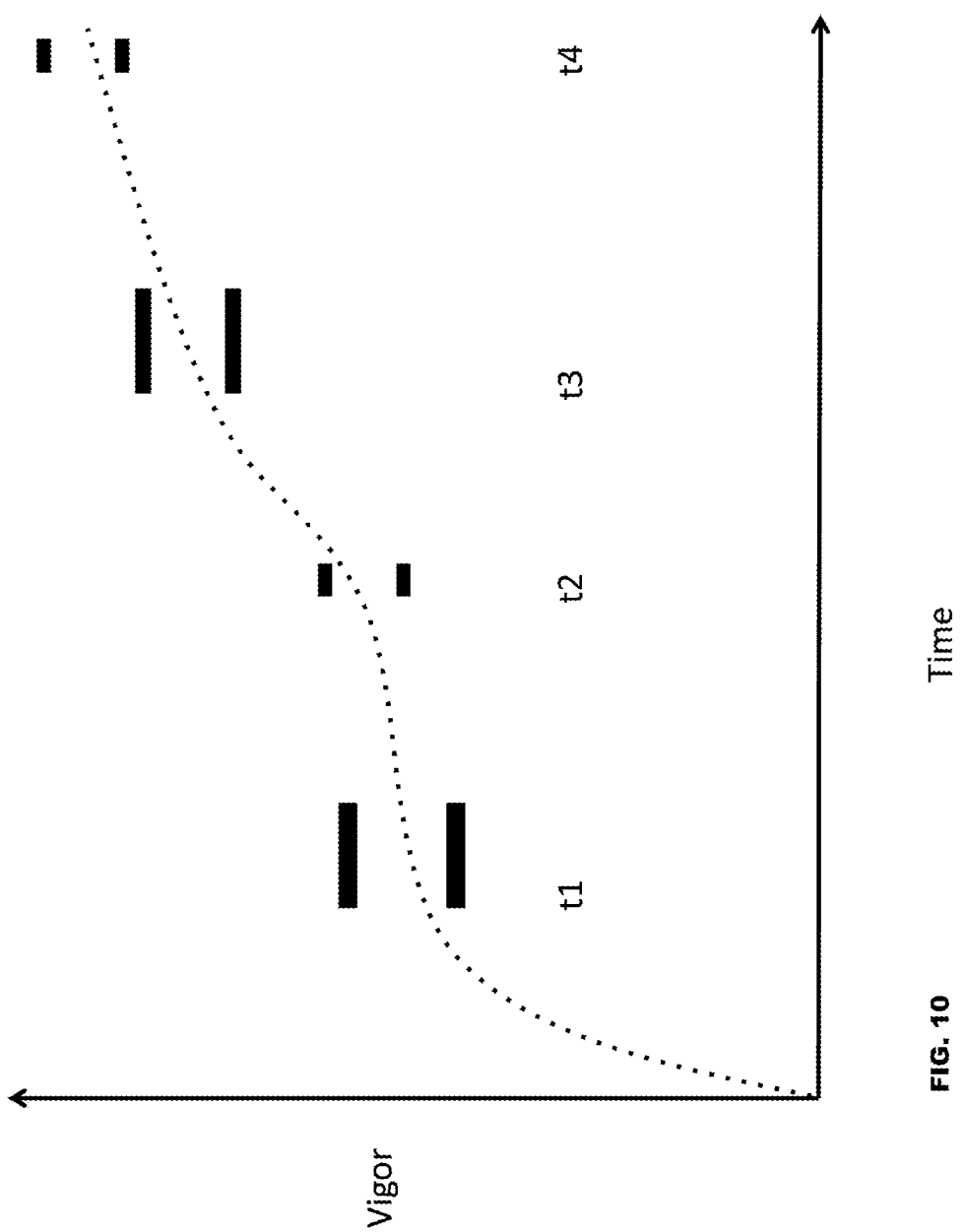
FIG. 10 represents an exemplary sequence of vigor and time values that form the basis of a hand hygiene standard that has vigorous motion to t1, gentle motion from t1 to t2, vigor again from t2 to t3, and mild vigor from t3 to t4.

Another embodiment entails linking profiles of vigor over time to comply with a more complex standard. For example, a standard may be generated that requires periods of vigorous motion interspersed with defined periods of stillness. A combination of threshold vigor levels and times may be established for such a profile. Referring to FIG. 10, a trajectory of vigor is established that requires vigorous motion to meet a first threshold by time t1, then a period with little or no motion until t2, a second vigorous phase until t3, and a subsequent period that requires motion less vigorous motion until t4. As known by those of ordinary skill in the art of hygiene training, a haptic, auditory, or visual feedback cue may be employed to indicate whether the target vigor ranges are being achieved by a person whose hand hygiene technique is being evaluated.

Static or time-gated thresholds for vigor, rocking angle, or combinations thereof may be articulated for any hygiene protocol according to the methods described herein. According to such methods, profiles of vigor and rocking angle are recorded for events that both comply and do not comply with the protocol, and differences between the profiles are defined to distinguish whether or not subsequent hand hygiene events are compliant.

Figure 11:
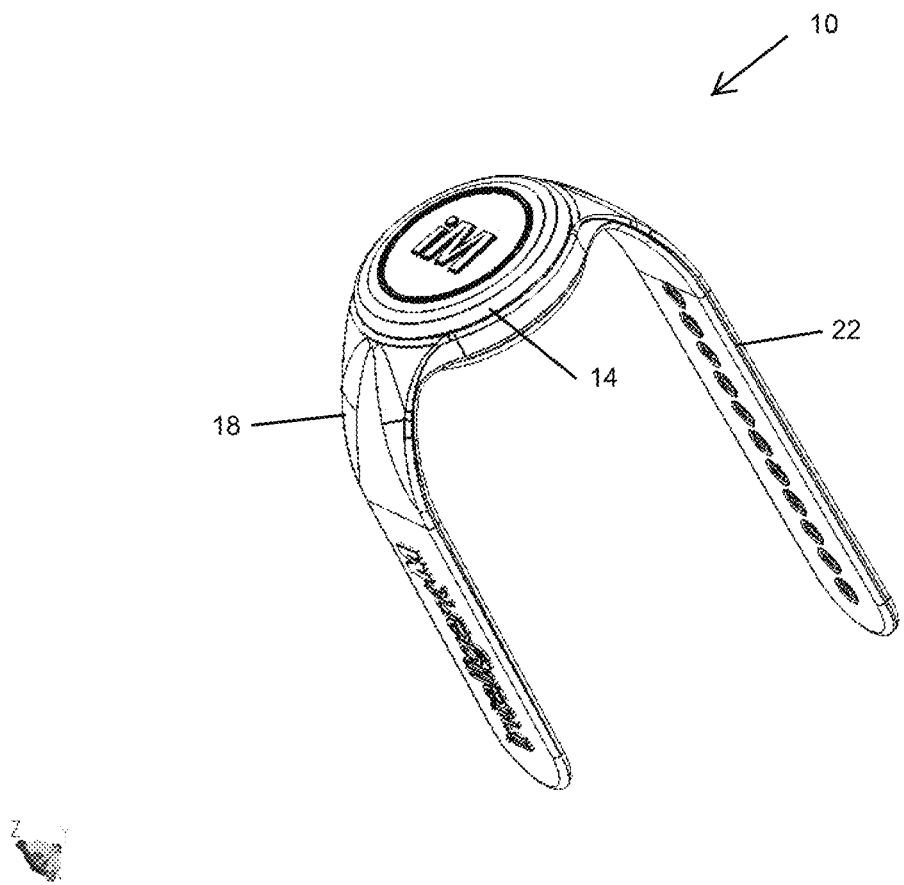
FIG. 11 illustrates a device for measuring compliance of a hand hygiene event with a predetermined standard according to one embodiment.

FIG. 11 illustrates a device 10 for measuring compliance of a hand hygiene event with a standard according to one embodiment of the present invention. As illustrated in FIG. 11, the device 10 is configured for application to a human wrist or arm. In one embodiment, the device 10 includes a housing 14, a first securement strap 18 coupled to and extending from one side of the housing 14, and a second securement strap 22 coupled to and extending from another side of the housing 14. The first strap 18 and the second strap 22 are arranged relative to the housing 14 and each other such that the straps 18, 22 can be coupled together to removably couple the device 10 to the user's wrist or arm. In other embodiments, only one securement strap can be used to removably couple the device 10 to a user's wrist or arm or entirely other configurations or means of securement can be used as known by those of skill in the art.

Figure 12:
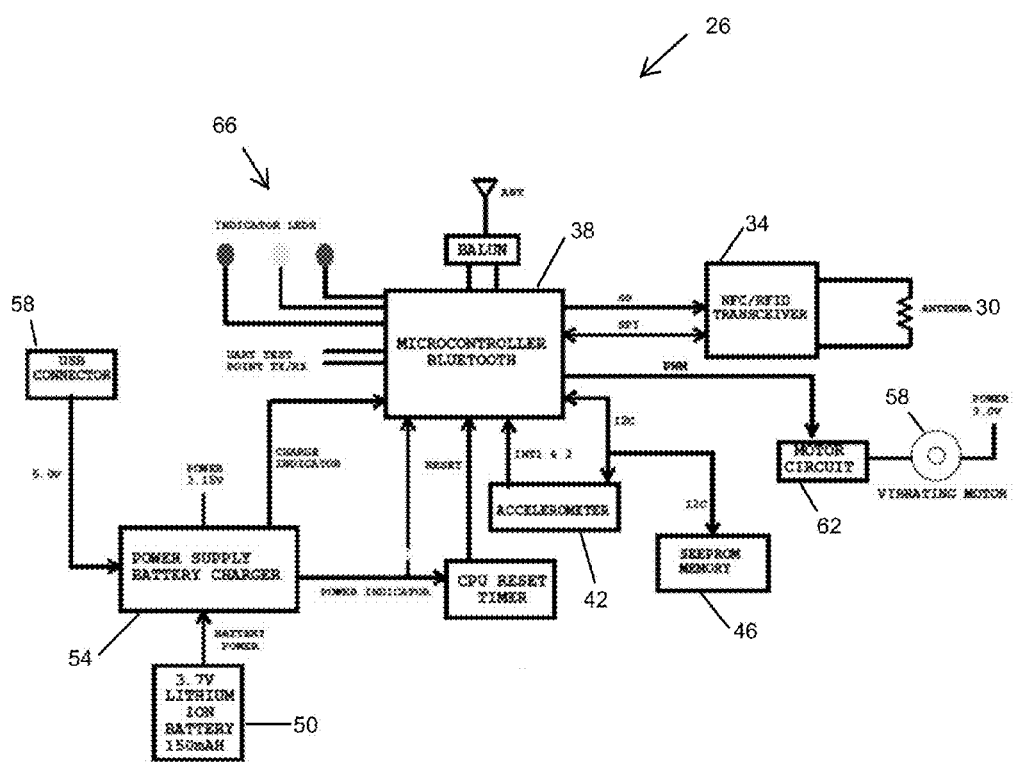
FIG. 12 illustrates a block diagram of an electronics module of the device shown in FIG. 11.

The housing 14 supports an electronics module 26 as illustrated in FIG. 12. The electronics module 26 includes an antenna 30 that detects a hygiene event when the antenna 30 is in proximity to a passive Radio Frequency Identification Device ("RFID") tag affixed to a soap or sanitizer dispenser (more details discussed below). The electronics module 26 also includes a RFID transceiver 34 (e.g., ST Microsystems model STRFNFCA circuit), which electronically communicates with the antenna 30. The RFID transceiver 34 electronically communicates with a microcontroller 38, which upon receiving a signal from the RFID transceiver 34, initiates acquisition of acceleration data from an accelerometer 42 and stores the acceleration values in memory 46 (e.g., random access memory (RAM) and/or non-volatile storage). The accelerometer 42 is structured and arranged to measure the multi-dimensional (x, y, z) acceleration, $\vec{a} = (a_x, a_y, a_z)$ of movement of the device 10 and, further, to transmit multi-dimensional acceleration $(a_x, a_y, a_z)$ data to the microcontroller 38. The microcontroller 38 is uniquely programmed to initiate a process (e.g., execute at least one application, algorithm, driver program, and the like, and also receive, store, and perform mathematical operations on stored acceleration data) to determine whether the user has complied with a hygiene standard such as a hand washing/sanitizing standard. An exemplary accelerometer is the Freescale Semiconductor model MMA8653FCR1, and an exemplary microcontroller is the Texas Instruments CC2541F256RHAR. Power to the electronics module 26 is supplied by a replaceable or rechargeable battery 50 through a charging circuit 54 connected to a power source 58.

The electronics module 26 also includes a motor 58 with appropriate motor circuitry 62 to provide a vibration to the housing 14. The vibration sensed by the user can indicate compliance or non-compliance with a standard. The electronics module 26 can also include one or more light emitting devices (e.g., LEDs or other illumination devices) 66 that, alternatively or in addition to the vibration, can be triggered to provide a visual signal to the user to indicate compliance or non-compliance with a standard. In other constructions, the device 10 can include an acoustic transducer to provide an audible alert to the user to indicate compliance or non-compliance with a predetermined hand hygiene standard.

In an alternative construction, and in lieu of local processing of the stored acceleration data (and determining vigor values and/or rocking angle values) by the microcontroller 38, the device 10 can be structured and arranged to provide external wireless communication to a remote processing device or receiving device, which will be discussed in greater detail below. For uploading to a cloud-based server, the communication device can be adapted to communicate wirelessly via a multitude of media, including but not to, for example, WiFi, Bluetooth, Zigbee, or other compatible communication protocols.

Figure 13:
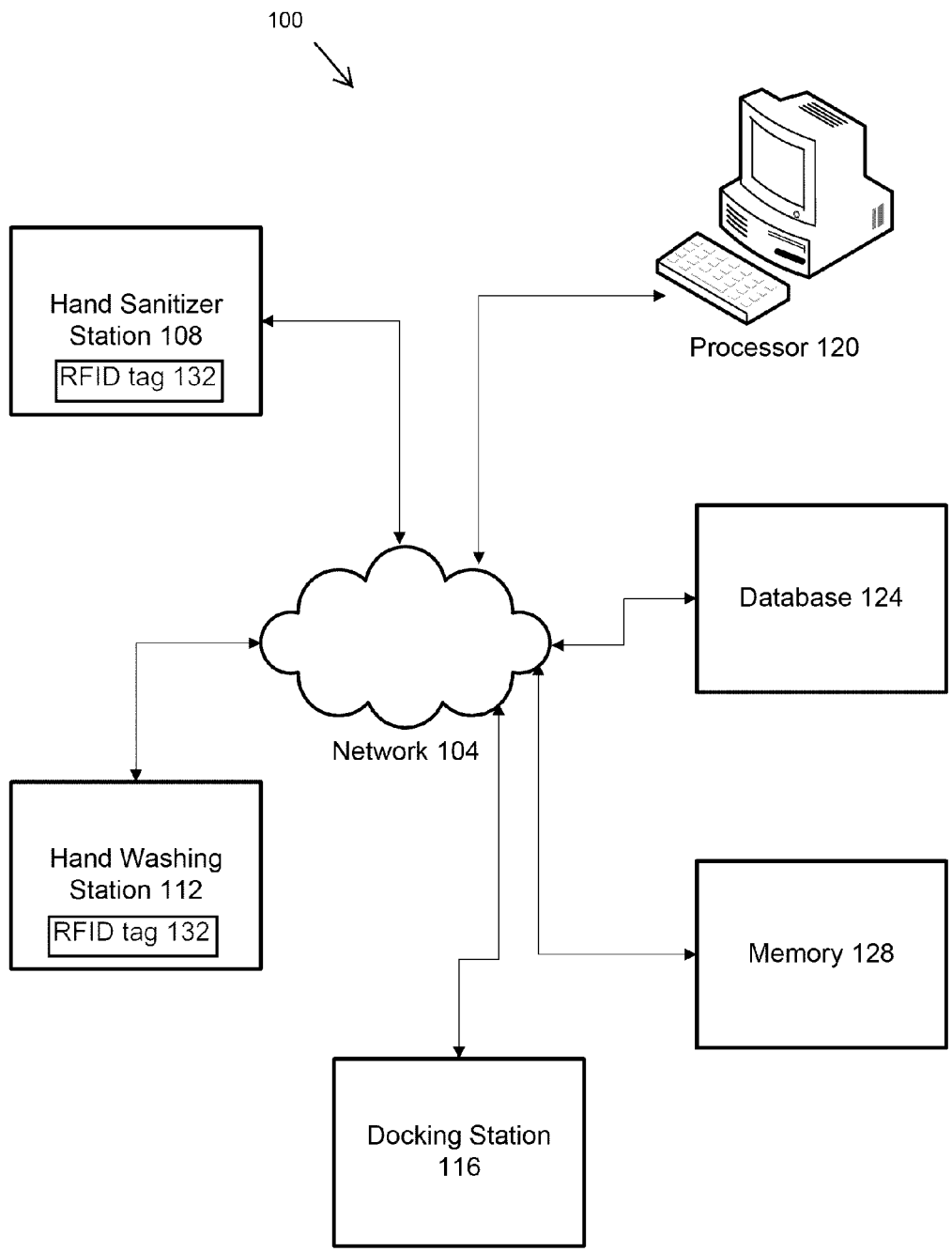
FIG. 13 is a schematic illustration of a system for measuring compliance of a hand hygiene event with a predetermined standard according to one embodiment.

FIG. 13 illustrates a system 100 for monitoring hand hygiene compliance with a predetermined hand hygiene standard. The system 100 includes a network 104, a plurality of hand sanitizer stations 108, a plurality of hand washing stations 112, a docking station 116, a processor 120, a database 124, and a memory 128. The docking station 116 retains multiple devices 10 and charges the devices 10 so they are ready for use. A user removes one of the devices 10 and applies it to his or her wrist. The user also correlates the device 10 to their personal identification by entering a unique device identification code or other indicia into the processor 120 or moving the device 10 near their name badge, which the device 10 reads and stores in memory 46. All subsequent hand hygiene events are then coded or tagged or identified with the particular user. Other methods of correlating the user to a particular device 10 are well known to persons of ordinary skill in the art and are contemplated herein.

Each of the hand sanitizer stations 108 and each of the hand washing stations 112 include a unique passive RFID tag 132 that transmits a signal to the environment in response to a probe signal from the transceiver 34 in device 10. The signal includes unique information such as the particular location or other identifying information of the hand sanitizer stations 108 or the hand washing stations 112. When a user, and thus the device 10, come within proximity to one of the hand sanitizer stations 108 or hand washing stations 112, the antenna 30 of the device 10 detects the RFID signal from the RFID tag 132, acquires the unique identification of the RFID tag 132, and stores the RFID tag identification into memory 46. The hand hygiene event that occurs at the station 108 or 112 is then linked to the RFID tag identification.

Depending on the type of RFID tag detected by the antenna 30, the microcontroller 38 initiates a hand washing program or a hand sanitizing program stored in memory in the microcontroller 38. The microcontroller 38 initiates acquisition of acceleration measurements from the accelerometer 42 and stores the acceleration measurements in memory 46 while the user is washing or sanitizing his or her hands. During or upon termination of the user's hand washing or sanitizing activity, the microcontroller 38 reads the acceleration measurements from memory 46 and determines vigor values and/or rocking angle values for each of the acceleration measurements.

If the vigor values (or a sampling thereof) meet a threshold that indicates compliance with a predetermined hand hygiene standard then a vibrating signal is conveyed through the motor circuit 62 to a vibrating motor 58 to indicate compliance with the established standard. Similarly, if the rocking angle values (or a sampling thereof) meet a threshold that indicates compliance with a predetermined standard then a vibrating signal is conveyed through the motor circuit 62 to a vibrating motor 58 to indicate compliance with the standard. Additionally, if the vigor values (or a sampling thereof) meet a threshold and the rocking angle values (or a sampling thereof) meet a threshold that indicates compliance with a predetermined standard then a vibrating signal is conveyed through the motor circuit 62 to a vibrating motor 58 to indicate compliance with the standard. Alternatively, or in addition to the vibration, a haptic signal may be conveyed by one or more light emitting diodes 66 or an acoustic transducer.

With respect to vibration, the microcontroller 38 can be programmed in numerous ways. For example, if only the vigor values meet the threshold, a single vibration can be generated to indicate to the user that their hand hygiene event is in compliance with a standard. As another example, if only the rocking angle values meet the threshold, two vibrations can be generated to indicate to the user that their hand hygiene event is in compliance with a standard.

If the vigor values and the rocking angle values do not meet the respective thresholds, then the hand hygiene event does not comply with the predetermined hand hygiene standard. As such, three vibrations can be generated to indicate to the user that their hand hygiene event is not in compliance with the standard. In another construction, if the hand hygiene event is not in compliance with the standard, the motor 58 can continue to vibrate to alert the user to go back and conduct remedial hand washing/sanitizing until there is compliance with the standard.

The user wears and uses the device 10 throughout his or her shift. At the end of the shift, the device 10 is returned to and plugged into the docking station 116 for charging, data uploading, data downloading, and application updates. More specifically, during the user's shift, the microcontroller 38 records, stores, and reports the data locally on the device 10. However, after the device 10 is re-docked in the docking station 116, the microcontroller 38 and the external communication device upload all stored data, including records of compliant and noncompliant hand hygiene events, to processor (or a cloud-based storage and application server) 120 and/or database 124, while any firmware or application updates are applied to the applications, algorithms, driver programs, and the like disposed in the microcontroller 38. The processor (or cloud-based storage and application server) 120 compiles the data looking for trends, missed hygiene opportunities, and compliance issues. The processor (or cloud-based storage and application server) 120 also uses data from a plurality of users to calculate a specific hand hygiene compliance percentage for a particular department or for the entire facility.

The docking station 116 communicates with the processor 120, which is structured and arranged to store and to execute applications, algorithms, driver programs, and the like that control device 10. For example, the processor 120 can, through the docking station 116, initiate remote diagnostics, upload collected data to a remote, cloud-based server upon re-docking, and, as necessary, download remote software and firmware updates. The processor 120 is also capable of using the data to prepare reports of compliance and non-compliance.

The methods described herein can be practiced with any form of accelerometer affixed to the hand, wrist, or forearm or from acceleration inferred from captured video frames that record hand motion.

Various features and advantages of the invention are set forth in the following claims.

What is claimed is:

1. A device for monitoring hand hygiene, the device comprising:
   a housing configured to be worn on a user's wrist, the housing including an accelerometer configured to measure acceleration vectors, $\vec{a}(t) = \vec{a}$, of the user's wrist projected along three linearly independent axes of motion; and
   a processing unit in communication with the accelerometer and configured to
      receive a plurality of the acceleration vector measurements taken over a period of time during a hand hygiene event carried out by the user,
      determine rocking angle values from the plurality of acceleration vector measurements by calculating $$r(t) = \cos^{-1}\left(\frac{\overrightarrow{a(t)}}{|a(t)|} \cdot \left(\frac{\overrightarrow{a(t)}}{|a(t)|}\right)\right),$$

the rocking angle values each being a scalar quantity,
compare the rocking angle values to one or more rocking angle thresholds established at preselected times based on a hand hygiene standard,
determine if one or more of the rocking angle values meets the one or more rocking angle thresholds, and
alert the user to a result of the comparison of the rocking angle values to the one or more rocking angle thresholds.

2. The device of claim 1, wherein the processing unit is further configured to alert the user if the one or more rocking angle thresholds are not satisfied.

3. The device of claim 2, further comprising a motor coupled to the housing, and wherein the alert to the user is a vibration provided by the motor.

4. The device of claim 1, further comprising a motor coupled to the housing, and wherein the alert to the user is a vibration provided by the motor.

5. The device of claim 1, wherein the hand hygiene standard is the World Health Organization's consensus standard for hand hygiene.

6. The device of claim 1, wherein the processing unit is further configured to alert the user if the one or more rocking angle thresholds are satisfied.

7. The device of claim 1, further comprising a RFID transceiver configured to read a RFID signal generated by a RFID tag affixed to a sanitizer station or a soap station.

8. The device of claim 1, wherein the one or more rocking angle thresholds are based on the user.

9. A system for monitoring hand hygiene, the system comprising:
   a plurality of hand hygiene stations, each station including a RFID tag having a unique identification;
   a device worn on a user's wrist, the device including a RFID tag reader and an accelerometer to measure acceleration vectors, $\vec{a}$; and
   a computer processor configured to
      receive the acceleration vectors, $\vec{a}$ from the device associated with a hand hygiene event at one of the hand hygiene stations,
      determine rocking angle values associated with the user's hand hygiene event from the acceleration vectors, $\vec{a}$, the rocking angle values each being a scalar quantity,
      determine if the rocking angle values associated with the hand hygiene event satisfies one or more rocking angle thresholds established at preselected times,
      transmit a first notification to the user if the hand hygiene event satisfies the one or more rocking angle thresholds, and transmit a second notification to the user if the hand hygiene event does not satisfy the one or more rocking angle thresholds.

10. The system of claim 9, wherein the hand hygiene event satisfies a standard for hand hygiene if a sampling of the rocking angle values satisfies the one or more rocking angle thresholds.

11. A method of evaluating compliance with a hygiene standard, the method comprising:

measuring acceleration vectors, $\vec{a}$, with an accelerometer applied to one or more of hands, wrists, or forearms during events that comply with the standard;

measuring acceleration vectors, $\vec{a}$, with an accelerometer applied to one or one or more of hands, wrists, or forearms during events that do not comply with the standard;

determining at least one rocking angle value by calculating $$r(t) = \cos^{-1}\left(\frac{\vec{a(t)}}{|a(t)|} \cdot \left(\frac{\vec{a(t)}}{|a(t)|}\right)\right)$$

for compliant events;

determining at least one rocking angle value by calculating $$r(t) = \cos^{-1}\left(\frac{\vec{a(t)}}{|a(t)|} \cdot \left(\frac{\vec{a(t)}}{|a(t)|}\right)\right)$$

for non-compliant events, the rocking angle values each being a scalar quantity; and comparing at least one of the rocking angle values for compliant events and rocking angle values for non-compliant events; and establishing one or more rocking angle thresholds at preselected times based on the comparison to establish whether compliance is achieved in subsequent events.

12. The method of claim 11 wherein the standard is the World Health Organization's consensus standard for hand hygiene technique.

13. The method of claim 10 wherein the standard is the World Health Organization's consensus standard for hand hygiene technique.

* * * * *